_United States Patent_ [19]

Green et al.

[11] Patent Number: 4,946,970

[45] Date of Patent: Aug. 7, 1990

[54] SUPPRESSION OF TRIMELLITIC ANHYDRIDE DUST

[75] Inventors: Michael R. Green, Geneva; Chang M. Park; Adel B. Abdul-Malek, both of Naperville, all of Ill.

[73] Assignee: Amoco Corporation, Chicago, Ill.

[21] Appl. No.: 279,430

[22] Filed: Dec. 2, 1988

[51] Int. Cl.$^5$ ............................................ C07D 307/77
[52] U.S. Cl. .................................... 549/245; 549/203
[58] Field of Search ................................ 549/203, 245

[56] References Cited

U.S. PATENT DOCUMENTS 4,208,433  3/1979  Darham et al. .................... 426/69
4,490,511  2/1981  Li et al. ............................. 525/507

FOREIGN PATENT DOCUMENTS 0292131  11/1988  European Pat. Off. .

OTHER PUBLICATIONS

Sorokin et al., "Reaction of Allyl Gylcidyl Ether with Trimellitic Anhydride", Chemical Abstracts, vol. 75, p. 292, (1971).

Tmenov et al., "Esterification of Trimellitic Anhydride by N-Octyl Alcohol", Chemical Abstracts, vol. 88, p. 116, (1978).

_Primary Examiner_—Mukund J. Shah
_Assistant Examiner_—C. L. Cseh
_Attorney, Agent, or Firm_—Gunar J. Blumberg; William H. Magidson; Ralph C. Medhurst

[57] ABSTRACT

There is provided a trimellitic anhydride composition having a reduced tendency to form trimellitic anhydride dust which composition comprises trimellitic anhydride treated with at least one organic compound wherein the organic compound is both liquid and substantially non-volatile at normal ambient temperatures and pressures. There is also provided a method for suppressing dust emitted from trimellitic anhydride which method comprises treating the trimellitic anhydride with the aforementioned organic compounds.

37 Claims, No Drawings

SUPPRESSION OF TRIMELLITIC ANHYDRIDE DUST

BACKGROUND OF THE INVENTION

1. Field of the Invention

This invention relates to the control of dust that is emitted from trimellitic anhydride. More particularly, this invention relates to the suppression of dust emitted from trimellitic anhydride by treating the trimellitic anhydride with an organic compound.

2. Prior Art

Trimellitic anhydride (TMA) is a useful chemical. It is an ideal chemical intermediate for a wide variety of chemicals and polymers. TMA is used in the manufacture of vinyl plasticizers, which can be used in electrical wire insulation, refrigerator gasketing, automotive padding and upholstery, washable sheeting, and pool liners. TMA is used in water-soluble alkyd coatings. It is used in the production of high-temperature polymers, such as amide-imide polymers. TMA is used as a curing agent for epoxy resins. In addition, its derivatives are used in various specialty applications, such as dye intermediates, heavy duty detergents, agricultural chemicals, and pharmaceuticals. However, TMA, particularly finely-divided TMA, is extremely difficult to handle because it emits a relatively large amount of dust. TMA dust can produce sensitization effects when inhaled.

Since much of the exposure to TMA dust occurs during the handling of TMA flakes, e.g., emptying TMA containers and/or during the production of TMA, a suitable method for suppressing airborne TMA dust particles is desired.

Various techniques have been used to suppress dust. For example, in U.S. Pat. No. 2,222,370, Mori disclosed a method for preventing and laying dust in coal mines by spraying the coal mine workings with a mixture or emulsion of petroleum oil and water, the water being present in an amount sufficient to make the oil spray noninflammable.

In U.S. Pat. No. 2,399,464, Butcher taught an improved liquid spraying agent adapted to inhibit the surface dusting of the soil in playgrounds, training camps, and dirt walks. The stable liquid dust-laying composition comprised a low-viscosity, low-volatility petroleum distillate oil, naphthenic acid, a wetting agent consisting essentially of a sodium salt of a sulfonated higher alcohol, water, and a germicide.

In U.S. Pat. No. 2,423,449, Heald, et al, disclosed treating soap to reduce dust-forming and lumping tendencies by spraying soap particles with a heavy mineral oil fraction.

In U.S. Pat. No. 2,585,026, Moen, et al, taught the reduction of dust produced by grain during handling by applying to the grain an emulsion of water and mineral oil.

In U.S. Pat. No. 3,913,637, Taylor taught the use of a liquid material such as white mineral oil to reduce the dust in a solid premix concentrate for addition to animal and poultry feed, the concentrate consisting essentially of gentian violet, a selective fungicidal mold inhibitor of "Candida albicaus," and inert ingredients.

In U.S. Pat. No. 4,276,308, Ito, et al, disclosed using a polybutene sticking agent in the preparation of granules containing a carboxylate, the granules being used safely as an effective wood preservative composition.

In Japanese Patent Publications Nos. 80037521, 50053538, and 56059701, there is taught a powdery agricultural agent giving less dusting, which powdery agricultural agent is prepared by mixing the active ingredient with a powdery inorganic carrier and polybutene or polyisobutene.

In U.S. Pat. No. 4,208,433, Darham, Jr., et al, disclosed the use of an oleaginous vehicle, such as corn oil, unrefined cottonseed oil, and soya oil, in the adsorption of dust into whole grain seeds to eliminate grain warehouse explosions, reduce fire hazards, and improve environmental conditions for humans.

In U.S. Pat. No. 4,490,511, Li, et al, disclosed a low-dusting anhydride curing agent blend for epoxy resins, which blend comprised a solid acid anhydride, TMA, and from 1 wt. % to about 10 wt. % normally liquid anhydride. The liquid anhydride was selected from methyl hexahydrophthalic anhydride, nadic methyl anhydride, and dodecyl succinic anhydride. The TMA flakes can be pre-wetted or the finely-divided TMA powder can be post-wetted with the liquid anhydride to provide the TMA with a greatly reduced dusting tendency.

There has now been found a method for suppressing dust emitted from TMA, which method employs the application of an organic compound to the TMA that does not appreciably affect the TMA in a deleterious manner and is selected from materials that are not liquid anhydrides.

SUMMARY OF THE INVENTION

There is provided a method for suppressing dust emitted from TMA, which method comprises treating said TMA with at least one organic compound wherein the organic compound is both liquid and substantially non-volatile at normal ambient temperatures and pressures. Treating is carried out by spraying the TMA, mixing the organic compound directly into the TMA or applying a solution of the organic compound dissolved in a volatile solvent.

There is also provided a stabilized TMA composition which emits a reduced amount of airborne dust. The composition comprises TMA and an organic compound, the TMA being present in an amount within the range of about 90 wt. % to about 99.999 wt. % and the organic compound being present in an amount within the range of about 0.001 wt. % to about 10 wt. %, each amount being based on the weight of the composition.

DESCRIPTION AND PREFERRED EMBODIMENTS

In view of the dusting tendency of TMA and the possible sensitization effect of TMA dust when inhaled, a suitable method for suppressing dust emitted from TMA is needed. A new method has been developed and this method is the subject of the present invention. The method for suppressing dust emitted from trimellitic anhydride comprises treating the TMA with an organic compound wherein the organic compound is both liquid and substantially nonvolatile at normal ambient temperatures and pressures. Such organic compounds are characterized by their ability to reduce the amount of air-borne dust that is emitted from the TMA and by their ability not to affect deleteriously the TMA or products made with the TMA. Suitable organic compounds are those organic compounds that are both liquid and substantially non-volatile at normal ambient temperatures and pressures. Preferred compounds are hydrocarbons, esters, mineral oils, white oils, polybutenes or hydrogenated polybutenes, alcohols and poly-alpha-olefins. Particularly preferred compounds are white oil, polybutenes and hydrogenated polybutene, 2-ethyl hexanol and tri-octyl-trimellitate (TOTM).

The hydrocarbon materials suitable for reducing TMA dust are those organic compounds comprising hydrogen and carbon atoms and may be linear, branched, saturated or unsaturated, aromatic or combinations of the above. It is preferred that these hydrocarbon compounds be liquid and substantially non-volatile at normal ambient temperatures and pressures.

A white oil is a highly refined lubricating oil fraction which has a colorless, water-white appearance. It is also odorless and tasteless and is essentially free of aromatic hydrocarbons, sulfur, and nitrogen. It has a color of +30 Saybolt and possesses a low absorbance of ultraviolet light. Typical white oils are prepared by means of a catalytic hydrogenation treatment of a lubricating oil fraction which has been dewaxed and/or solvent extracted and are used for cosmetics and certain medicinal purposes. A typical white oil for use as a dust-suppressing agent is a 55 white oil that can be obtained from Amoco Oil Company and is identified as Amoco White Mineral Oil No. 5-NF. Such white oil has a sulfur content that is less than 2 ppm (wt) and a nitrogen content that is less than 1 ppm (wt) and is approximately 50% paraffins and 50% naphthenes.

While white oil is a preferred compound of this invention for suppressing TMA dust because it is odorless and colorless and does not impart undesirable characteristic to the treated TMA, other refined oils both mineral and from animal and vegetable sources are also suitable dust suppressing agents of the invention.

Another suitable organic compound for suppressing TMA dust comprises viscous polybutenes having a number average molecular weight in the range of about 250 to about 500 and a viscosity at 38° C. (100° F.) in the range of about 4 to about 1,100 centistokes. Such polybutenes are essentially water white, resistant to oxidation by light and heat, nondrying and thermally decompose without residue at a temperature above about 275° C. Such polybutenes may be obtained by the polymerization of a refinery butenes stream in the presence of a Friedel-Crafts-type catalyst. The refinery butenes stream, often identified as the "C$_4$" or "B-B" (Butanes-Butenes) olefin stream from petrochemical cracking units, is a convenient source of isobutylene, 1-butene, and cis- and trans-2-butene. The polybutenes comprise isobutylene-butene copolymers made up of high molecular weight mono-olefins (95 to 100%) and isoparaffins. Polybutenes suitable for use as a dust-suppressing agent are commercially available. Typical examples of suitable polybutenes are the Indopol L-4, Indopol L-10, Indopol L-14, Indopol L-50, and Indopol L-100 polybutenes provided by Amoco Chemical Company.

Moreover, hydrogenated polybutenes are suitable dustsuppressing agents for use with TMA. Hydrogenated polybutenes are available commercially. For example, they may be obtained from Amoco Chemical Company under the tradename Panalane.

The poly-alpha-olefin materials made by the dimerization, trimerization or oligomerization of alpha-olefins, such as C$_{10}$- alpha olefin, followed by a hydrogenation step to remove unsaturations are also suitable organic compounds of this invention for suppressing TMA dust. These materials are available in a variety of viscosities and molecular weights however they are all characterized by having excellent chemical inertness and excellent viscosity properties. They find wide use as synthetic lubricants. They are liquid and substantially non-volatile at normal ambient conditions. They are available from, for example, Gulf Chemical Company. The poly-alpha-olefins made from the dimerization and trimerizations of a C$_{10}$-alpha olefin is a particularly suitable poly-alphaolefin compound suitable for suppressing TMA dust.

Alcohols and mixtures of alcohols are also organic compounds useful for suppressing TMA dust formation. In order to be effective the alcohol should be both substantially non-volatile and liquid at normal ambient temperatures and pressures. A liquid alcohol is easier to apply to the TMA and also may provide a coating action to control dust formation. Suitable alcohols are the mono-hydroxylic alcohols that have six or more carbon atoms and may be linear, branched, cyclic, heterocyclic or aromatic. Examples of alcohols in this category, without intending to limit the alcohols useful for this invention, include the hexanols, e.g., 1-hexanol, 2-hexanol, cyclohexanol; the heptanols, the octanols, e.g. 2-ethylhexanol, iso-octanol and 1-octanol. Diols such as ethylene glycol or propylene glycol are also suitable alcohols. These diols are liquid and substantially non-volatile at normal ambient temperatures and pressures. Other diols with three or more carbon atoms are also suitable. Alcohols with three or more hydroxyl groups are also suitable alcohols, i.e. glycerol and the so called polyols. A particularly preferred alcohol is 2-ethylhexanol since 2-ethylhexanol is widely used for preparing esters of trimellitic anhydride or acid. It can be obtained commercially from Eastman Chemicals, Ashland Chemical, Shell Chemical and Union Carbide.

Esters and mixtures of esters are also organic compounds useful for reducing TMA dust. The esters that are useful are those that are liquid and substantially non-volatile at normal ambient temperatures and pressures. Particularly suitable esters are those esters made from aromatic mono-, di- and poly-carboxylic acids. Esters made from aliphatic carboxylic acids are also useful. These acids may be mono-, di- or polY-carboxylic. They may be linear, branched, cyclic, saturated or unsaturated. Adipic and oleic acid are examples of these acids.

The particularly preferred esters useful for suppressing TMA dust are the esters of acids selected from the group consisting of terephthalic acid, isophthalic acid, phthalic acid, trimellitic acid, pyromellitic acid, a naphthalene carboxylic acid, a naphthalene dicarboxylic acid, oleic acid and adipic acid.

The ester organic compounds of this invention are prepared by esterifying the acid components with an alcohol. The alcohol may be any alcohol. Suitable alcohols, without intending to limit the choice of alcohol, are for example, methanol, ethanol, propanols, butanols, 2-ethylhexanol, isooctanol, glycols or polyols or mixtures of these or other alcohols. The alcohols can be linear, branched, cyclic or aromatic.

Tri-octyl-trimellitite (TOTM), prepared by esterifying trimellitic acid or trimellitic anhydride with 2-ethylhexanol is a particularly preferred ester for reducing TMA dust formation.

For the purposes of this invention normal ambient temperatures and pressures means those normally experienced atmospheric conditions that exist outdoors or indoors such as in a chemical or manufacturing plant environment. In a preferred embodiment of this invention, the organic compound should be a liquid when it is applied to the TMA and should remain liquid. This facilitates application and dust-suppression, respectively. However, it is not a requirement that the organic compound contemplated by this invention be liquid at ambient temperature and pressure. They may also be solid and can be heated or dissolved in a solvent to facilitate application to the TMA. Furthermore it is not a requirement that the organic compounds of this invention exist as liquids throughout the entire range of normal ambient temperatures and pressures. The organic compounds of this invention useful for suppressing TMA dust may be liquids in only part of the temperature and pressure range of normal ambient temperatures and pressures.

Pursuant to the method of the present invention, the TMA is contacted with the organic compound in order to coat the surface of the TMA with the organic compound. Generally, the TMA is present in the form of powder, flakes, crystals, briquettes, pellets, or pastilles. Preferably, the TMA is present in the form of flakes.

The organic compound can be applied to the TMA in one of three ways. Preferably, the TMA is contacted with the organic compound by spraying the organic compound on the surface of the TMA. Alternatively, agitation can be used and the organic compound is stirred directly into the solid TMA material. Thirdly, a diluent is added to the organic compound in order to achieve a more uniform application of the compound on the TMA. The organic compound and diluent combination is applied either by spraying or by direct stirring. The diluent is removed subsequently. A suitable diluent may be any volatile solvent that is miscible with the organic compound.

The treating should be such as to put on the surface of the TMA an amount of organic compound that is within the range of about 10 ppm by weight (0.001 wt. %) to about 100,000 ppm by weight (10 wt. %); suitably, within the range of about 50 ppm by weight (0.005 wt. %) to about 20,000 ppm by weight (2 wt. %); and, preferably, within the range of about 100 ppm by weight (0.01 wt. %) to about 2,000 ppm by weight (0.2 wt. %), based on the weight of the treated TMA.

According to the present invention, there is also provided a stabilized TMA composition having a reduced tendency to form TMA dust, which composition comprises TMA treated with at least one organic compound wherein the organic compound is both liquid and substantially non-volatile at normal ambient temperatures and pressures and the TMA being present in an amount within the range of about 90 wt. % to about 99.999 wt. %, based on the total weight of the composition, and the organic compound being present in an amount within the range of about 0.001 wt. % to about 10 wt. %, based on the total weight of the composition. This composition is prepared conveniently by the method of the present invention.

The following examples are presented to facilitate a better understanding of the method and composition of the present invention and to illustrate the present invention and are not intended to limit the scope of the present invention.

EXAMPLE I

A qualitative test was performed to show the effectiveness of the method of the present invention.

An untreated sample of TMA flakes, Sample No. 1, was tumbled for 1 hr at 90-120 rpm in a stainless steel mixing jar equipped with inner baffles. The tumbled TMA was collected and placed in a transparent glass jar suitable for viewing clearly the contents of the jar.

To a second sample of TMA, Sample No. 2, were added 500 ppm of the white oil. Sample No. 2 was then tumbled under the same conditions as Sample No. 1. Visual comparison between the two TMA samples was made in regard to the amount of airborne TMA dust generated when the samples were shaken and opened in a fume hood. Dust was observed exiting the untreated sample, Sample No. 1. On the other hand, the treated TMA sample, Sample No. 2, had comparatively very little TMA dust emanating from the jar.

EXAMPLE II

Several tests were conducted to determine the amount of airborne TMA dust that would result when a selected TMA sample was subjected to agitation. The test system was made up of an agitation source for shaking the TMA sample and a collection device for collecting airborne TMA dust. The agitation source was a sieve shaker and was employed to cause dust to become airborne when the TMA sample was shaken. Once airborne, the TMA dust was collected in the collection device, which consisted of a small portable vacuum pump connected to a Millipore matched weight aerosol filter cassette. The matched weight filter cassette consisted of a set of two filters of equal weight in series. Filters of the same filter cassette were manufactured to weigh within ±0.0001 gm of each other. The TMA dust was collected on the first filter and the difference in weight between the first and second filters was equivalent to the amount of TMA dust that was collected on the first filter.

Each test was conducted in the following manner. The TMA sample (100 gm) was placed in a 16-oz jar having an 89 mm cap. The jar was agitated by the sieve shaker and the airborne TMA dust was sampled for 1 hr. The setting for the vacuum pump was 1.2 liters/min. All weighings were performed on a laboratory analytical balance. Samples Nos. 3, 4, and 5 were run as blanks (air samples), i.e., there was no TMA in the sample jar. Samples Nos. 6 and 7 were untreated TMA. Samples Nos. 8 and 9 were TMA treated with 1 000 ppm white oil while Samples Nos. 10 and 11 were TMA treated with 1,000 ppm trioctyltrimellitate (TOTM).

The results of these tests are presented hereinbelow in Table I.

TABLE I

TMA Dust Suppression

| Sample No. | Sample Description | Weight, gm | | |
|---|---|---|---|---|
| | | 1st Filter | 2nd Filter | Delta Weight |
| 3 | air | 0.0443 | 0.0443 | 0.0000 |
| 4 | air | 0.0452 | 0.0451 | 0.0001 |
| 5 | air | 0.0450 | 0.0450 | 0.0000 |
| 6 | TMA | 0.0486 | 0.0450 | 0.0036 |
| 7 | TMA | 0.0475 | 0.0450 | 0.0025 |
| 8 | TMA + white oil (1,000 ppm) | 0.0519 | 0.0512 | 0.0007 |
| 9 | TMA + white oil (1,000 ppm) | 0.0488 | 0.0487 | 0.0001 |
| 10 | TMA + TOTM (1,000 ppm) | 0.0515 | 0.0509 | 0.0006 |
| 11 | TMA + TOTM (1,000 ppm) | 0.0447 | 0.0452 | −0.0005 |

The tests made with air samples, i.e., Samples Nos. 3, 4, and 5, demonstrated that no weight gain occurred when air was the sample. This suggested that the environmental dust was negligible under the test application and only TMA dust was being collected when TMA samples were subjected to the test. Both the white oil and TOTM reduced or suppressed the dust of the TMA.

EXAMPLE III

A series of tests was conducted to confirm the results of the tests performed in Example I and minimize the effects of experimental and instrumental error. In these tests, 125-gm samples were used, the sampling time was extended to 5 hr, and the vacuum setting was maintained at 2.8 l/min. In addition, the amounts of the material added to suppress the dust were varied. The test system was the same as that employed in the tests conducted in Example II.

The results of these tests are presented hereinbelow in Table II.

TABLE II

TMA Dust Suppression[1]

| Sample No. | Treatment Agent | Amount, ppm | Weight, gm 1st Filter | 2nd Filter | TMA Dust |
|---|---|---|---|---|---|
| 12 | — | — | 0.1595 | 0.0445 | 0.1150 |
| 13 | TOTM | 100 | 0.0518 | 0.0438 | 0.0080 |
| 14 | TOTM | 250 | 0.0568 | 0.0452 | 0.0116 |
| 15 | TOTM | 500 | 0.0546 | 0.0457 | 0.0089 |
| 16 | TOTM | 750 | 0.0464 | 0.0447 | 0.0017 |
| 17 | TOTM | 1,000 | 0.0488 | 0.0447 | 0.0041 |
| 18 | — | — | 0.0846 | 0.0445 | 0.0401 |
| 19 | OIL[2] | 100 | 0.0464 | 0.0443 | 0.0021 |
| 20 | OIL[2] | 250 | 0.0456 | 0.0449 | 0.0007 |
| 21 | OIL[2] | 750 | 0.0488 | 0.0482 | 0.0006 |
| 22 | OIL[2] | 1,000 | 0.0461 | 0.0457 | 0.0004 |
| 23 | P[3] | 1,000 | 0.0458 | 0.0451 | 0.0007 |

[1] For 125-gm sample at vacuum setting of 2.8 l/min and setting time of 5 hr
[2] OIL is white oil
[3] P is Panalane (hydrogenated polybutenes)

These data suggest that as the amount of dust-suppressing agent is increased, the amount of detected dust is decreased. In addition, the data indicate that white oil has better dust-suppressing ability than TOTM.

EXAMPLE IV

These tests were conducted in order to ascertain whether the method for dust suppression of the present invention would interfere with TMA end-use applications. Untreated TMA and TMA treated with either white oil or TOTM were esterified with 2-ethylhexanol. Color evaluations of each of the esterification products were made via a spectrophotomeric method identified as the ΔE method for TMA, wherein the total color difference between a solution of 3N NaOH and a solution composed of 5 gm of TMA dissolved in 30 ml of 3N NaOH was obtained. The ΔE value is related to the color of the TMA product in the 400 to 700 nm wavelength range as measured by a spectrophotometer.

The results of these color measurements are presented hereinbelow in Table III.

TABLE III

TMA Dust Suppression Applications

| Sample No. | Treatment | Cook time, hr | ΔE | FEC[1] | CEC[2] |
|---|---|---|---|---|---|
| 24 | — | 5 | 2.43 | 30 | 45 |
| 25 | 0.1 wt % oil[3] | 4 | — | 30 | 45 |

TABLE III-continued

TMA Dust Suppression Applications

| Sample No. | Treatment | Cook time, hr | ΔE | FEC[1] | CEC[2] |
|---|---|---|---|---|---|
| 26 | 0.1 wt % TOTM | 4.75 | — | 30 | 45 |

[1] FEC is final ester color
[2] CEC is crude ester color
[3] Oil is white oil

These data indicate that neither the white oil nor the TOTM caused color problems in esterifications of TMA with 2-ethylhexanol. The sample treated with white oil and the sample treated with TOTM gave no observable difference in the crude ester color or final ester color of TOTM, when compared to the untreated TMA sample.

EXAMPLE V

Additional tests were conducted to determine whether the dust-suppressing agent would be detrimental to the TMA end-use applications. These tests were conducted according to the procedure described hereinabove in Example IV, with the exception that 10,000 ppm of white oil or 10,000 ppm (wt) of TOTM were employed.

The results of the color measurements are presented hereinbelow in Table IV.

TABLE IV

TMA Dust Suppression Applications

| Sample No. | Treatment | Cook time, hr | ΔE | FEC[1] | CEC[2] |
|---|---|---|---|---|---|
| 27 | — | 4.5 | 3.03 | 35 | 40 |
| 28 | 1 wt % oil[3] | 4.5 | 3.02 | 30 | 45 |
| 29 | 1 wt % TOTM | 4.0 | 3.08 | 35 | 45 |

[1] FEC is final ester color
[2] CEC is crude ester color
[3] Oil is white oil

Again, neither the white oil nor the TOTM caused color problems in esterifications of TMA with 2-ethylhexanol.

EXAMPLE VI

The trimellitate esters described in Table III were used as plasticizers for preparing clear polyvinyl chloride (PVC) sheets. The sheets were evaluated in a variety of testing procedures to determine if the 0.1 percent TOTM or 0.1 percent white oil added to the TMA would cause performance deficiencies in end use products.

The performance test data given in Table V demonstrates that these materials do not cause performance deficiencies in PVC sheets. The performance test data is equivalent for the treated and untreated TMA. The performance tests include: Tensile Properties, Activated Carbon Volatility, Soapy Water Extraction, Mineral Oil Extraction, HumiditY CompatibilitY, Roll Spew-Exudation, Shore A Hardness and Brittleness Temperature.

TABLE V

Performance Evaluation of Clear Polyvinyl Chloride Sheets Formulated With TOTM Plasticizer Made From TMA Treated With White Oil or TOTM

| | TMA Treatment (TOTM Sample No.) | | |
|---|---|---|---|
| | None (24) | 0.1% Oil (25) | 0.1% TOTM (26) |
| Tensile Properties | | | |
| Tensile Strength (PSI) | 3387 | 3321 | 3319 |
| 100% Modulus (PSI) | 2255 | 2322 | 2235 |
| 300% Modulus (PSI) | 3194 | 3180 | 3039 |
| % Elongation | 349 | 351 | 347 |
| Activated Carbon Volatility-Percent Weight Loss (90° C.) | | | |
| 24 hours | 0.5 | 0.5 | 0.5 |
| 48 hours | 0.6 | 0.6 | 0.6 |
| Soapy Water Extraction-Percent Weight Loss (90° C.) | | | |
| 48 Hours | 0.2 | 0.2 | 0.2 |
| 72 Hours | 0.2 | 0.2 | 0.2 |
| Mineral Oil Extraction-Percent Weight Loss (70° C.) | | | |
| 24 hours | 2.4 | 2.3 | 2.3 |
| Humidity Capatibility-Exudation (90° C.) | | | |
| 7 days | None | None | None |
| Roll Spew-Exudation (Room Temperature) | | | |
| 96 hours | None | None | None |
| Shore A Hardness | | | |
| Initial | 94 | 94 | 93 |
| 10 seconds | 89 | 89 | 88 |
| Brittleness Temperature | | | |
| Degrees C | −22 | −24.9 | −22.8 |

EXAMPLE VII

The trimellitate esters described in Table III were used to formulate UL 105° C. polyvinyl chloride electrical wire insulation materials. These PVC materials were evaluated in a variety of testing procedures to determine if the 0.1 percent TOTM or 0.1 percent white oil added to the TMA would result in performance problems in end use products.

The performance test data, given in Table VI, shows that these materials do not cause performance problems in PVC wire insulation formulated with plasticizer made with treated TMA. The performance tests include: Initial tensile strength measurements, tensile strength measurements after seven days at 136° C., and the percent retention of tensile strength after the seven-day treatment.

TABLE VI

Performance Evaluation of Wire Insulation Formulated With TOTM Plasticizer Made From TMA Treated With White Oil or TOTM Dust Suppressant

| | TMA Treatment (TOTM Sample No.) | | |
|---|---|---|---|
| | None (24) | 0.1% Oil (25) | 0.1% TOTM (26) |
| Tensile Properties | | | |
| Tensile Strength (PSI) | 3424 | 3404 | 3319 |
| 100% Modulus (PSI) | 2358 | 2325 | 2342 |
| 300% Modulus (PSI) | 3109 | 3099 | 3000 |
| % Elongation | 363 | 363 | 353 |
| Aged 7 Days at 136° C. | | | |
| Tensile Strength (PSI) | 3596 | 3544 | 3461 |
| 100% Modulus (PSI) | 2683 | 2784 | 2712 |
| 300% Modulus (PSI) | 3315 | 3439 | 3336 |
| % Elongation (PSI) | 348 | 330 | 321 |
| Percent Retention | | | |
| Tensile Strength | 105 | 104 | 104 |
| 100% Modulus | 114 | 119 | 116 |
| 300% Modulus | 107 | 111 | 111 |
| % Elongation | 96 | 91 | 91 |

EXAMPLE VIII

The trimellitate esters described in Table IV were used as plasticizers to prepare clear polyvinyl chloride (PVC) sheets. These sheets were evaluated in a variety of testing procedures to determine if the 1.0 percent TOTM or 1.0 percent white oil added to the TMA would cause performance problems in an end use product. A treatment with 1 percent (10,000 PPM) TOTM or white oil represents a relatively high treat rate and if performance problems are to occur, they would be most apparent at these higher treat rates.

The performance data in Table VII demonstrates that the polyvinyl chloride sheets formulated with plasticizer made from TMA treated with 1 percent TOTM or 1 percent white oil are essentially equivalent to the base case where no TOTM or white oil was added to the TMA used to make the plasticizer.

TABLE VII

Performance Evaluation of Clear Polyvinyl Chloride Sheets Formulated With TOTM Plasticizer Made From TMA Treated With White Oil or TOTM Dust Suppressant

| | TMA Treatment (TOTM Sample No.) | | |
|---|---|---|---|
| | None (27) | 1.0% Oil (28) | 1.0% TOTM (29) |
| Tensile Properties | | | |
| Tensile Strength (PSI) | 3437 | 3551 | 3425 |
| 100% Modulus (PSI) | 2251 | 2398 | 2275 |
| 300% Modulus (PSI) | 3078 | 3209 | 3057 |
| % Elongation | 375 | 365 | 375 |
| Activated Carbon Volatility-Percent Weight Loss (90° C.) | | | |
| 24 hours | 0.6 | 0.7 | 0.5 |
| 48 hours | 0.6 | 0.9 | 0.6 |
| Soapy Water Extraction-Percent Weight Loss (90° C.) | | | |
| 48 Hours | 0.2 | 0.5 | 0.2 |
| 72 Hours | 0.3 | 0.5 | 0.3 |
| Mineral Oil Extraction-Percent Weight Loss (70° C.) | | | |
| 24 hours | 2.5 | 2.1 | 2.5 |
| Humidity Capatibility-Exudation (90° C.) | | | |
| 7 days | None | None | None |
| Roll Spew-Exudation (Room Temperature) | | | |
| 96 hours | None | None | None |
| Shore A Hardness | | | |
| Initial | 95 | 95 | 95 |
| 10 seconds | 91 | 91 | 92 |
| Brittleness Temperature | | | |
| Degrees C | −24.2 | −22.8 | −23.6 |

EXAMPLE IX

The trimellitate esters described in Table IV were used to formulate UL 105° C. polyvinyl chloride electrical wire insulation materials. These PVC materials were evaluated in a variety of testing procedures to determine if the 1.0 percent TOTM or 1.0 percent white oil added to the TMA would result in performance deficiencies in the end use product. A treatment with 1 percent (10,000 PPM) TOTM or white oil represents a relatively high treat rate and if performance problems are to occur, they would be most apparent at these higher treat rates.

The performance data in Table VIII demonstrate that the polyvinyl chloride wire insulation materials formulated with plasticizer made from TMA treated with 1 percent TOTM or 1 percent white oil are essentially equivalent to the base case material that was formulated with TOTM made from untreated TMA.

TABLE VIII

Performance Evaluation of Wire Insulation Formulated With TOTM Plasticizer Made From TMA Treated With White Oil or TOTM Dust Suppressant

| | TMA Treatment (TOTM Sample No.) | | |
|---|---|---|---|
| | None (27) | 1.0% Oil (28) | 1.0% TOTM (29) |
| Initial Tensile Properties | | | |
| Tensile Strength (PSI) | 3404 | 3668 | 3412 |
| 100% Modulus (PSI) | 2408 | 2595 | 2401 |
| 300% Modulus (PSI) | 3263 | 3392 | 3231 |
| % Elongation | 345 | 347 | 354 |
| Aged 7 Days at 136° C. | | | |
| Tensile Strength (PSI) | 3668 | 3777 | 3635 |
| 100% Modulus (PSI) | 2859 | 2973 | 2849 |
| 300% Modulus (PSI) | 3463 | 3517 | 3471 |
| % Elongation (PSI) | 340 | 335 | 333 |
| Percent Retention | | | |
| Tensile Strength | 107 | 103 | 106 |
| 100% Elongation | 119 | 115 | 118 |
| 300% Elongation | 106 | 104 | 107 |
| % Elongation | 98 | 96 | 94 |

EXAMPLE X

TMA treated with 0.1 percent (1000 PPM) TOTM and 0.1 percent white oil were also used to prepare water-borne alkyd and polyester resins that are used as coatings. There were no observable defects in appearance of the applied films, e.g., "fish eyes," craters or loss-of-gloss, and there were no differences in the physical performance properties of the coatings prepared with the treated TMA compared to coatings made with untreated TMA. These evaluations prove that the TMA treated with the organic compounds of this invention is acceptable for preparing water-borne coatings, a major end use for TMA.

What is claimed is:

1. A trimellitic anhydride (TMA) composition having a reduced tendency to form TMA dust which composition comprises solid TMA treated with at least one organic compound wherein said organic compound is applied to the surface of said solid TMA and wherein the organic compound is both liquid and substantially non-volatile at normal ambient temperatures and pressures and wherein the organic compound does not contain an anhydride functionality; the TMA being present in an amount within the range of about 90 wt. % to about 99.999 wt. %, based on the total weight of the composition, and the organic compound being present in an amount within the range of about 0.001 wt. % to about 10 wt. %, based on the total weight of the composition.

2. The composition of claim 1 wherein the organic compound comprises a hydrocarbon.

3. The composition of claim 1 wherein the organic compound comprises an ester.

4. The composition of claim 1 wherein the organic compound comprises mineral oil.

5. The composition of claim 1 wherein the organic compound comprises a white oil.

6. The composition of claim 1 wherein the organic compound comprises a polybutene.

7. The composition of claim 1 wherein the organic compound comprises a hydrogenated polybutene.

8. The composition of claim 1 wherein the organic compound comprises an alcohol.

9. The composition of claim 1 wherein the organic compound comprises a poly-alpha-olefin.

10. The composition of claim 3 wherein the ester is an ester of an acid selected from the group consisting of terephthalic acid, isophthalic acid, phthalic acid, trimellitic acid, pyromellitic acid, naphthalene carboxylic acid, oleic acid and adipic acid.

11. The composition of claim 1 wherein the organic compound comprises a vegetable oil.

12. The composition of claim 1 wherein the organic compound comprises an animal oil.

13. The composition of claim 8 wherein the alcohol is 2-ethylhexanol.

14. The composition of claim 3 wherein the ester is tri-octyl-trimellitate (TOTM).

15. The composition of claim 1 wherein the TMA is present within the range of about 98 wt. % to about 99.995 wt. %, based on the weight of the composition, and the organic compound is present in an amount within the range of about 0.005 wt. % to about 2 wt. %, based on the weight of the composition.

16. The composition of claim 1 wherein the TMA is present within the range of about 99.8 wt. % to about 99.99 wt. %, based on the weight of the composition, and the organic compound is present in an amount within the range of about 0.01 wt. % to about 0.02 wt. %, based on the weight of the composition.

17. A method for suppressing dust emitted from trimellitic anhydride (TMA), which method comprises treating solid TMA with at least one organic compound wherein the organic compound is both liquid and substantially non-volatile at normal ambient temperatures and pressures and wherein the organic compound does not contain an anhydride functionality and wherein said organic compound is applied to the surface of said solid TMA.

18. The method of claim 17 wherein said treating comprises contacting the TMA with the organic compound, the organic compound being stirred directly into the TMA by means of agitation.

19. The method of claim 17 wherein said treating comprises spraying the TMA with the organic compound.

20. The method of claim 17 wherein said treating comprises applying the organic compound to the TMA as a solution of the organic compound in a volatile solvent.

21. The method of claim 17 wherein the TMA is treated with the organic compound to provide on the TMA an amount of organic compound that is within the range of about 10 ppm (by weight) to about 100,000 ppm (by weight), based on the weight of treated TMA.

22. The method of claim 17 wherein the TMA is treated with the organic compound to provide on the TMA an amount of organic compound that is within the range of about 100 ppm (by weight) to about 2000 ppm (by weight), based on the weight of treated TMA.

23. The method of claim 17 wherein the organic compound comprises a hydrocarbon.

24. The method of claim 17 wherein the organic compound comprises an ester.

25. The method of claim 17 wherein the organic compound comprises mineral oil.

26. The method of claim 17 wherein the organic compound comprises white oil.

27. The method of claim 17 wherein the organic compound comprises a polybutene.

28. The method of claim 17 wherein the organic compound comprises a hydrogenated polybutene.

29. The method of claim 17 wherein the organic compound comprises an alcohol.

30. The method of claim 17 wherein the organic compound comprises a poly-alpha-olefin.

31. The method of claim 24 wherein the ester is an ester of an acid selected from the group consisting of terephthalic acid, isophthalic acid, phthalic acid, trimellitic acid, pyromellitic acid, naphthalene carboxylic acids, naphthalene dicarboxylic acids, oleic acid and adipic acid.

32. The method of claim 17 wherein the organic compound comprises a vegetable oil.

33. The method of claim 17 wherein the organic compound comprises an animal oil.

34. The method of claim 29 wherein the alcohol is 2-ethylhexanol.

35. The method of claim 24 wherein the ester is trioctyl-trimellitate.

36. A trimellitic anhydride (TMA) composition having a reduced tendency to form TMA dust which composition comprises solid TMA treated with at least one organic compound wherein said organic compound is applied to the surface of said solid TMA and wherein the organic compound is selected from the group consisting of hydrocarbons which are linear, branched, saturated, unsaturated, aromatic, or combinations thereof, white oils, refined mineral oils, refined vegetable oils, refined animal oils, viscous polybutenes having a number average molecular weight within the range of about 250 to about 500 and a viscosity at 38° C. (100° F.) within the range of about 4 to about 1,100 centistokes, hydrogenated polybutenes, poly-alphaolefin materials prepared by the dimerization, trimerization, or oligomerization of alpha-olefins followed by hydrogenation, alcohols selected from monohydroxylic alcohols having six or more carbon atoms, diols having two or more carbon atoms, and alcohols having three or more hydroxyl groups, and esters made from aromatic mono-, di-, and poly-carboxylic acids and aliphatic mono-, di, and polycarboxylic acids, said organic compound being both liquid and substantially non-volatile at normal ambient temperatures and pressures and not containing an anhydride functionality, said TMA being present in an amount within the range of about 90 wt. % to about 99.999 wt. %, based on the total weight of the composition, and said organic compound being present in an amount within the range of about 0.001 wt. % to about 10 wt. %, based on the total weight of the composition.

37. A method for suppressing dust emitted from trimellitic anhydride (TMA) which method comprises treating solid TMA with at least one organic compound wherein said organic compound is applied to the surface of said solid TMA and wherein said organic compound is selected from the group consisting of hydrocarbons which are linear, branched, saturated, unsaturated, aromatic, or combinations thereof, white oils, refined mineral oils, refined vegetable oils, refined animal oils, viscous polybutenes having a number average molecular weight within the range of about 250 to about 500 and a viscosity at 38° C. (100° F.) within the range of about 4 to about 1,100 centistokes, hydrogenated polybutenes, poly-alpha-olefin materials prepared by the dimerization, trimerization, or oligomerization of alpha-olefins followed by hydrogenation, alcohols selected from mono-hydroxylic alcohols having six or more carbon atoms, diols having two or more carbon atoms, and alcohols having three or more hydroxyl groups, and esters made from aromatic mono-, di-, and poly-carboxylic acids and aliphatic mono-, di-, and polycarboxylic acids, said organic compound being both liquid and substantially non-volatile at normal ambient temperatures and pressures and not containing an anhydride functionality.

* * * * *

UNITED STATES PATENT OFFICE
CERTIFICATE OF CORRECTION

Patent No. 4,946,970               Dated   August 7, 1990

Inventor(s)  Michael R. Green, Chang Man Park, & Adel B. Abdul-Malek

It is certified that error appears in the above-identified patent and that said Letters Patent is hereby corrected as shown below:

| Col. | Line | | |
|------|------|---|---|
| 1 | 30 | "emptYing" should read | --emptying-- |
| 3 | 26 | "approximatelY" should read | --approximately-- |
| 4 | 41-42 | "polY-carboxylic" should read | --poly-carboxylic-- |
| 5 | 5 | "TheY may" should read | --They may-- |
| 5 | 40 | "preferablY" should read | --preferably-- |
| 6 | 43 | "with 1 000" should read | --with 1,000-- |
| 8 | 65 | "HumiditY CompatabilitY" should read --Humidity Compatability-- | |

Signed and Sealed this

Seventeenth Day of September, 1991

*Attest:*

HARRY F. MANBECK, JR.

*Attesting Officer*   *Commissioner of Patents and Trademarks*